United States Patent
Wakabayashi et al.

(10) Patent No.: US 6,562,793 B2
(45) Date of Patent: May 13, 2003

(54) ANTIALLERGIC AGENT

(75) Inventors: Kazuyoshi Wakabayashi, Kanazawa (JP); Hiroyoshi Moriyama, Tokyo (JP)

(73) Assignee: We'll Corporation, Matto (JP)

( * ) Notice: Subject to any disclaimer, the term of this patent is extended or adjusted under 35 U.S.C. 154(b) by 0 days.

(21) Appl. No.: 10/000,713

(22) Filed: Oct. 31, 2001

(65) Prior Publication Data

US 2002/0086834 A1 Jul. 4, 2002

(30) Foreign Application Priority Data

Nov. 15, 2000 (JP) ........................ 2000-347600

(51) Int. Cl.[7] ..................... A61K 31/70; C07H 17/04
(52) U.S. Cl. .................... 514/27; 536/8; 424/195.1; 424/757; 435/200; 549/403
(58) Field of Search ................. 536/8; 424/195.1, 424/757; 435/200; 514/27; 549/403

(56) References Cited

U.S. PATENT DOCUMENTS 5,679,806 A * 10/1997 Zheng et al. ............... 549/403
5,990,291 A * 11/1999 Waggle et al. ................ 536/8

FOREIGN PATENT DOCUMENTS

JP   05170756   * 7/1993

OTHER PUBLICATIONS

Barnes et al., "Rationale for the use of Genistein–containing soy matrices in chemoprevention trials for breast and prostate cancer." Journal of Cellular Biochemistry, Suppl. 22, pp. 181–187, 1995.*
Harborne et al. "Plant Polyphenols: Flavonoids in genotypes of Primula Sinensis." Biochem. J. 78, 298–306, 1961.*
Buttiner et al. "Anticancer agents from Chilean plants, Cassia Obtusa." Rev. Latinoamer. Quim. 4(1), 8–14, 1973.*
Ishiguro et al. "Antipruritic effect of Flavonol and 1,4–Naphthoquinone derivatives from *Impatiens balsamina* L." Phytotherapy Research, vol. 11, 343–47, 1997.*
Budzianowski et al. "Microvascular protective activity of Flavonoid Glucuronides fraction from *Tulipa gesneriana*." Phytotherapy Research, 13, 166–68 (1999).*
Harborne, J. and Sherratt, H.S.A., *Biochem. J.*, vol. 78, 1961, pp. 298–306.

* cited by examiner

*Primary Examiner*—Samuel Barts
*Assistant Examiner*—Devesh Khare
(74) *Attorney, Agent, or Firm*—Price, Heneveld, Cooper, DeWitt & Litton

(57) ABSTRACT

A material containing a flavonoid glycoside represented by formula I as a major component has an in vivo antiallergic effect, which can be prepared in a large amount with a lower cost.

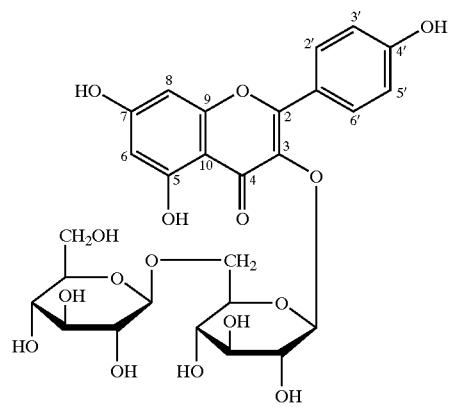

15 Claims, 4 Drawing Sheets

ANTIALLERGIC AGENT

BACKGROUND OF THE INVENTION

1. Field of the Invention

This invention relates to a flavonoid glycoside exhibiting an excellent antiallergic effect even in a small amount.

2. Description of the Prior Art

Flavonoids are a class of compounds which are widely distributed in the plant kingdom and have been known from long ago. A flavonoid is a modulator for germination and growth of a seed, as well as is believed to absorb ultraviolet rays in sunlight to protect internal tissues. In particular, it is known that a flavonoid protects and strengthen capillary vessels in human body.

SUMMARY OF THE INVENTION

One aspect of the present invention relates to a product comprising a food, drug or cosmetic and a flavonoid glycoside represented by formula I wherein the flavonoid glycoside is present in an antiallergenic effective amount.

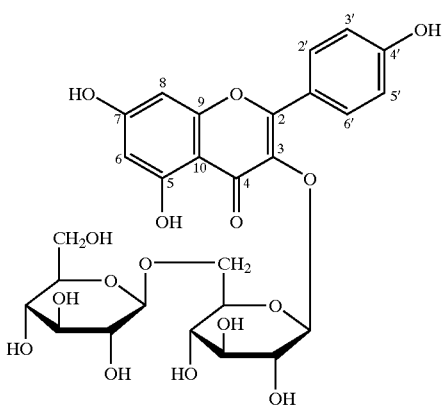

Another aspect of the present invention provides a method of inhibiting histamine release by administering to a mammal an antiallergenic effective amount of a flavonoid glycoside represented by formula I.

Yet another aspect of the present invention provides a method of obtaining a flavonoid glycoside represented by formula I by extracting the flavonoid glycoside from a plant in the Cassia genus.

DESCRIPTION OF THE PREFERRED EMBODIMENTS

Figure 1:
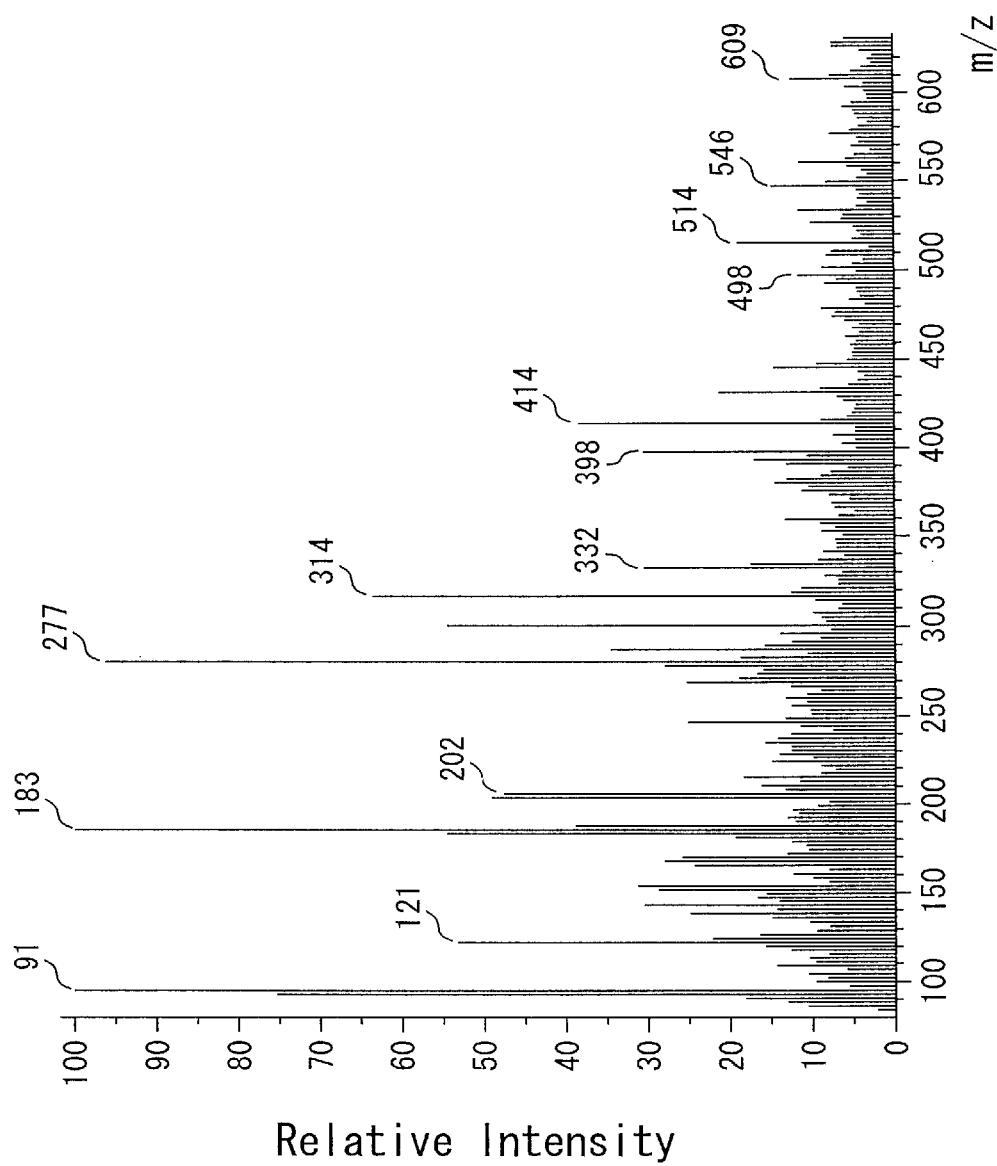
FIG. 1 shows a fast atom bombardment mass spectrum.

We have paid attention to such a flavonoid, in particular to the fact that plants in a genus of Cassia contain flavonoids exhibiting a variety of pharmacological actions. Thus, we have extracted flavonoids from Cassia plants. The isolated and purified compounds have then been investigated for their particular pharmacological actions.

Consequently, we have obtained a flavonoid glycoside represented by formula I from a Cassia plant.

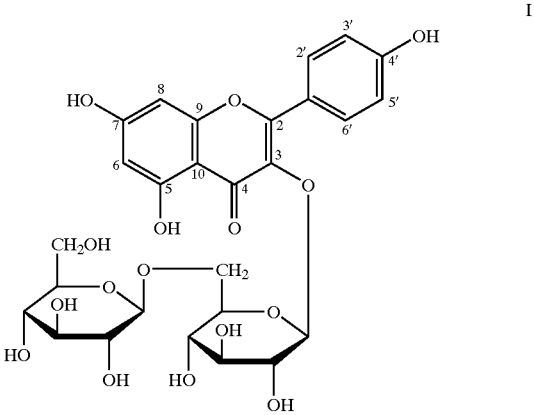

This compound was, however, a glycoside in which a disaccharide is attached to a hydroxide group at C-3 in a kind of flavonoid kaempferol, i.e., kaempferol 3-gentiobioside, which is a known compound (Harborne J. and Sherratt, H. S. A. Biochem J. 78, 298–306, 1961).

There have been, however, no reports describing that the flavonoid glycoside represented by formula I has an antiallergic effect and is effective even in a small amount. Thus, after further investigation, we have found that the flavonoid glycoside represented by formula I can be obtained from a plant other than those in Cassia genus, for example, Primula Sinesis, but the amount obtained is considerably smaller than that from a Cassia plant and that even for a Cassia plant, the flavonoid glycoside represented by formula I may be obtained in a smaller amount as a leaf grows from its young stage.

We have also found that the above compound is obtained in the highest amount from Candle bush (Latin name: *Cassia alata*) among plants in Cassia genus. Furthermore, experimental results show that a young leaf with a moisture content of about 8% contains the flavonoid glycoside represented by formula I in about 4.3% while a grown leaf contains it in less than about 1.8%.

The flavonoid glycoside represented by formula I according to this invention can be prepared by extracting a plant in the Cassia genus with water or an organic solvent such as alcohols and methanol and purifying the extract using any of known procedures including a variety of chromatographic techniques such as column chromatography used in separation or extraction of a plant component alone or in combination.

Any plant belonging to the Cassia genus may be utilized, and *Cassia alata* is particularly preferable. Any part of *Cassia alata* including leaves, stems, roots, buds, flowers and seeds may be used, and particularly young leaves may give the compound in the highest amount.

The flavonoid glycoside represented by formula I according to this invention exhibits an excellent antiallergic effect even in a small amount so that it may be advantageously used in the field of antiallergic agents. Furthermore, it may be collected from a plant in the Cassia genus; particularly young leaves of *Cassia alata* give a large amount of the compound which is freely soluble in water. The glycoside may be, therefore, used not only in foods and drinks including health foods and cosmetics as an antiallergic agent, but also in various drugs utilizing its antiallergic property.

An objective of this invention is to obtain a large amount of a compound exhibiting an antiallergic effect and to provide an antiallergic agent at a lower cost.

The flavonoid glycoside represented by formula I according to this invention has the following physical and chemical properties.

Appearance: Yellow powder

Molecular formula: $C_{27}H_{30}O_{16}$

Optical rotation: $[\alpha]_D$-43.9° (C=0.70, pyridine)

Fast atom bombardment mass spectrum (FIG. 1): m/z 609 (M-H)$^-$

Figure 2:
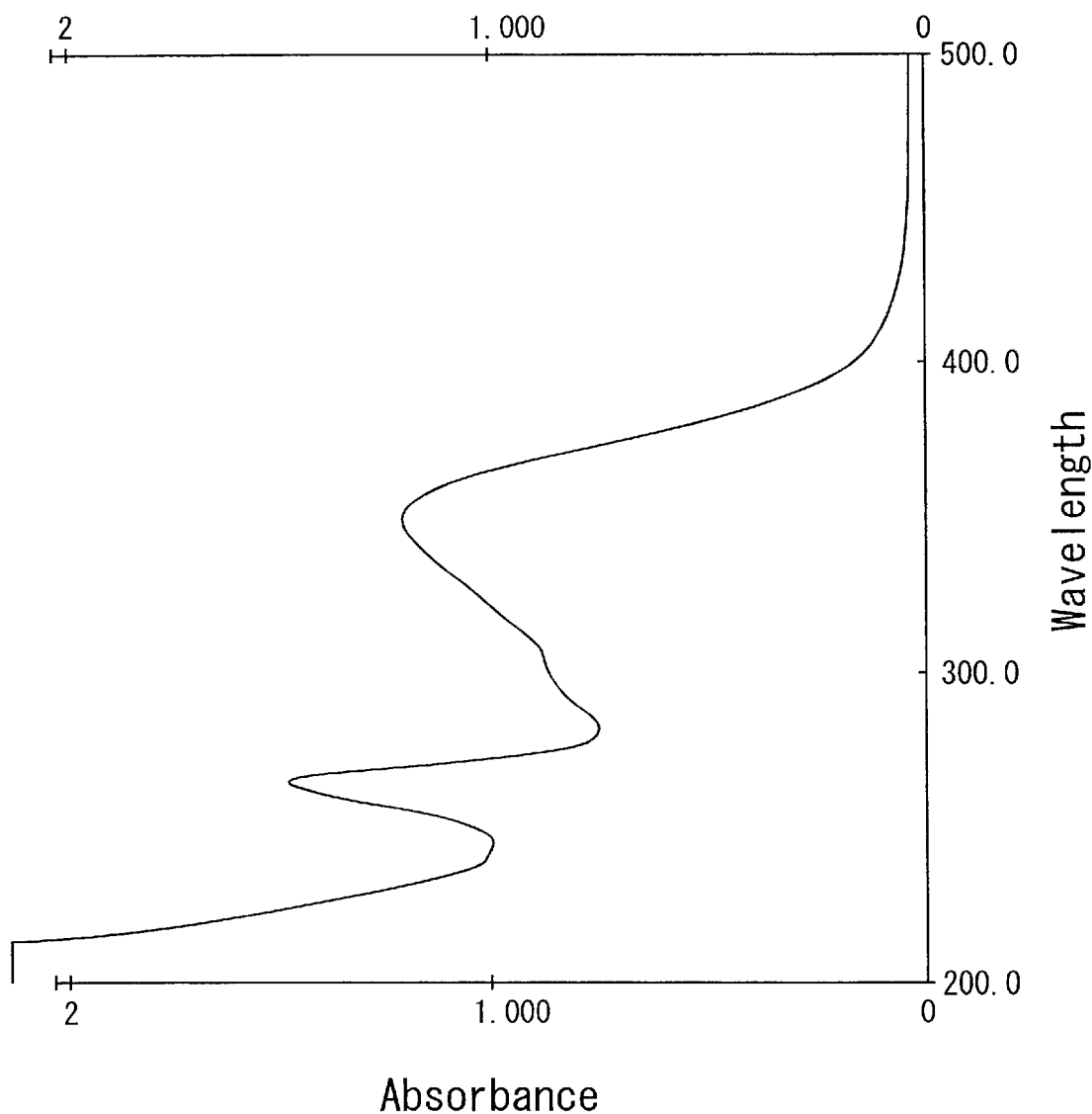
FIG. 2 shows an ultraviolet absorption spectrum.

Ultraviolet absorption spectrum (FIG. 2): $UV\lambda_{max}^{MeOH}$ nm: 266, 299sh, 349

Figure 3:
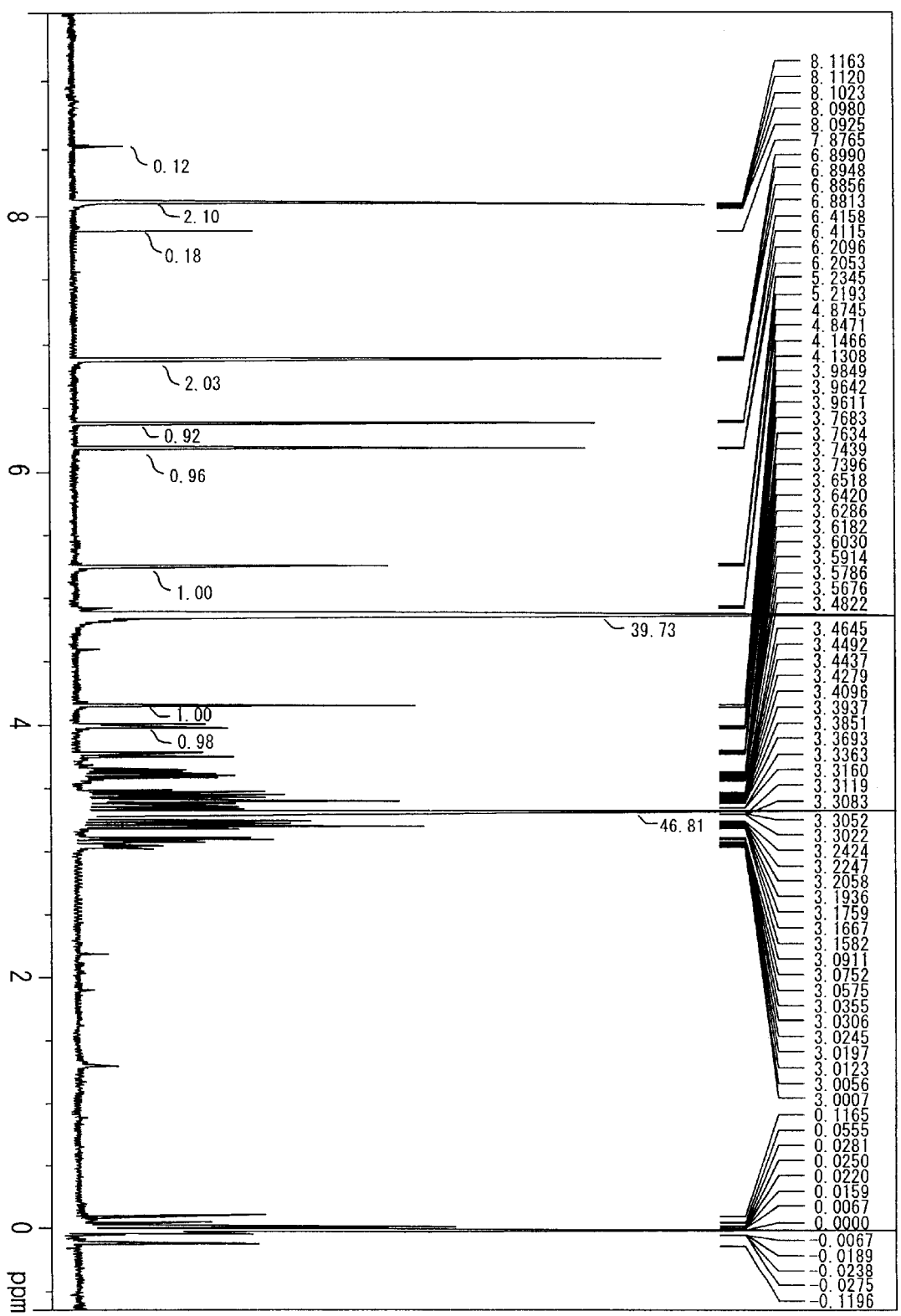
FIG. 3 shows a proton nuclear magnetic resonance spectrum.

Proton nuclear magnetic resonance spectrum (FIG. 3): δppm (270 MHz, DMSO-$d_6$):

8.10 (2H, d, J=9.0 Hz, H-2', 6'), 6.89 (2H, d, J=9.0 Hz, H-3', 5'), 6.41 (1H, d, J=2.0 Hz, H-8), 6.21 (1H, d, J=2.0 Hz, H-6), 5.22 (1H, d, J=7.5 Hz, H-1'), 4.14 (1H, d, J=8.0 Hz, H-1''')

Figure 4:
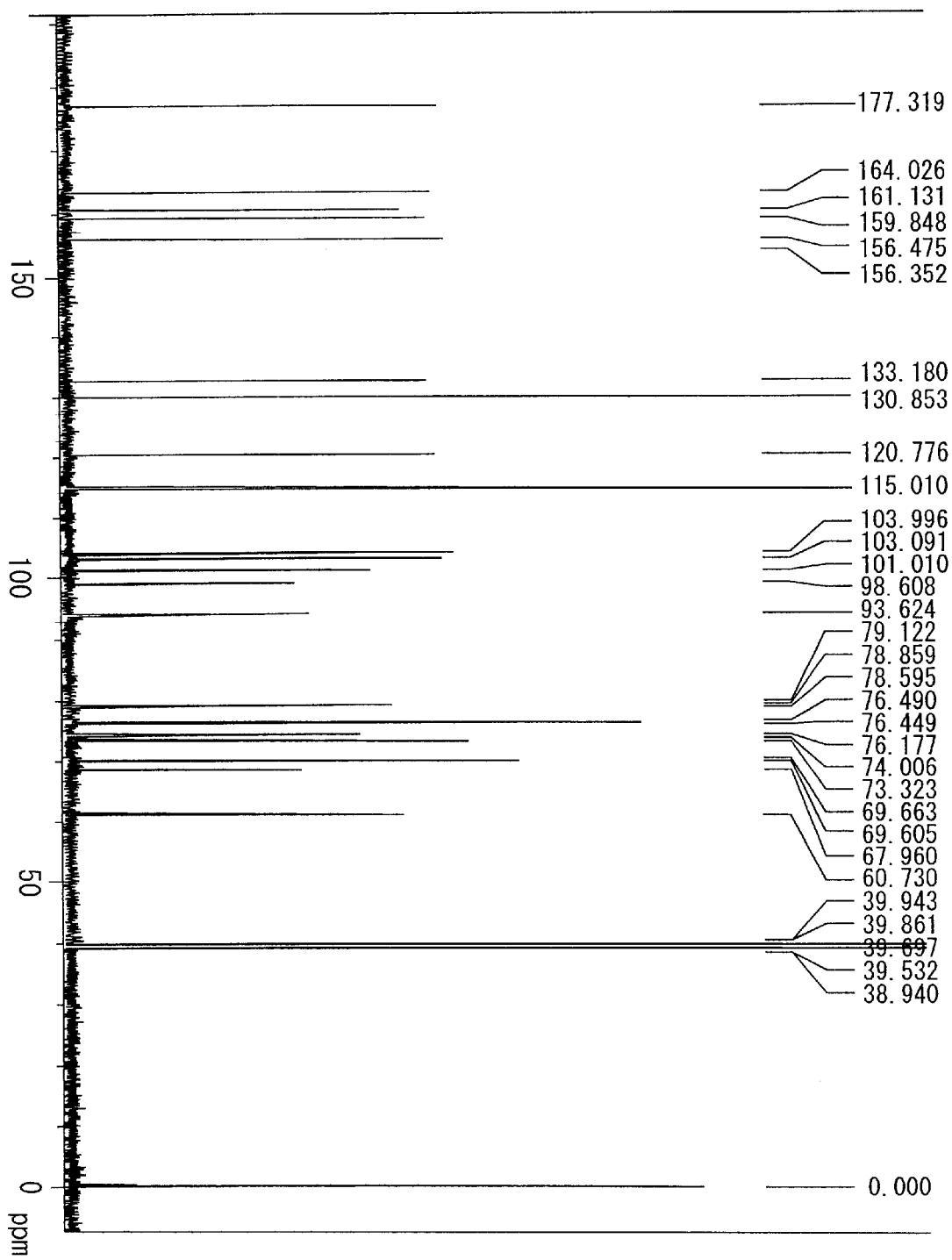
FIG. 4 shows a carbon nuclear magnetic resonance spectrum.

Carbon nuclear magnetic resonance spectrum (FIG. 4): δppm (500 MHz, DMSO-$d_6$):

156.48 (C-2), 133.18 (C-3), 177.32 (C-4), 161.13 (C-5), 98.60 (C-6), 164.03 (C-7), 93.62 (C-8), 156.35 (C-9), 104.00 (C-10), 120.78 (C-1'), 130.85 (C-2'), 115.01 (C-3'), 159.85 (C-4'), 115.01 (C-5'), 130.85 (C-6'), 101.01 (C-1''), 73.32 (C-2''), 76.44 (C-3''), 69.61 (C-4''), 78.86 (C-5''), 67.96 (C-6''), 103.09 (C-1'''), 74.00 (C-2'''), 69.66 (C-4'''), 76.18 (C-5'''), 60.73 (C-6''')

Hydrolysis products: a saccharide fraction was spotted on a TLC plate silica gel 60 F254 and gave an $R_f$ value corresponding to that for a standard (gentiobiose). Furthermore, an aglycone was identified by comparing it with a standard (kaempferol) using high performance liquid chromatography (HPLC) and ultraviolet absorption spectrometry (UV).

From the above physical and chemical properties and other studies, the flavonoid glycoside represented by formula I according to this invention was identified as kaempferol 3-gentiobioside (kaempferol 3-0 [β-D-glucopyranosyl-(1→6)-β-D-glucopyranoside]), having the following chemical structure:

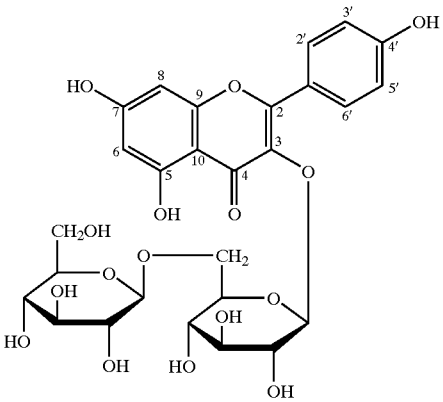

The following examples will describe a compound according to this invention using, for example, the Cassia genus.

EXAMPLE 1

Dried leaves of *Cassia alata* are extracted with 50% methanol, and the solvent is evaporated. After evaporation, the residue is dissolved in distilled water for collecting water-insoluble components. The solution is adsorbed by Diaion HP20, and eluted with methanol to give a 80% methanol fraction. The fraction is purified by column chromatography using Sephadex LH-20 and then by high performance liquid chromatography. The product is recrystallized to give kaempferol 3-gentiobioside. Its physical and chemical properties have been already shown and its chemical structure is represented by formula I.

EXAMPLE 2

Standard solutions of kaempferol 3-gentiobioside in different concentrations of 12.0 μg/mL, 24.0 μg/mL and 48.0 μg/mL were analyzed three times for each solution to provide a calibration curve, where a correlation coefficient was 0.9998. Then, 0.1 g of a young leaf of *Cassia alata* with a moisture content of about 8% was mixed with 100 mL of 50% methanol, and the mixture was incubated at 80° C. for one hour with stirring. Then, to the extract was added 50% methanol to 100 mL. After microfiltration, the material obtained was assayed for kaempferol 3-gentiobioside by high performance liquid chromatography with the following conditions.

Apparatus: Liquid chromatograph

Pump: Pump LC-10AD (Shimazu)

Detector: SPD-10AV (Shimazu)

Printer: C-R8A CHROMATOPAK (Shimazu)

Column: YMC-Pack ODS-A (YMC)

Mobile phase: Diluted glacial acetic acid (1→80): acetonitrile (4:1) (used after degassing by ultrasonication)

Flow rate: 1.0 mL/min

Temperature: Room temperature

Detection: UV at 349 nm

Chart speed: 1 cm/min

Injection volume: 10 μL

The assay showed that the young leaf of *Cassia alata* contained about 4.3% of pferol 3-gentiobioside.

EXAMPLE 3

Standard solutions of kaempferol 3-gentiobioside in different concentrations of 12.0 g/mL, 24.0/mL and 48.0/mL were analyzed three times for each solution to provide a calibration curve, where a correlation coefficient was 0.9998. Then, 0.1 g of a mature leaf of *Cassia alata* with a water content of about 8% was mixed with 100 mL of 50% methanol, and the mixture was incubated at 80° C. for one hour with stirring. After microfiltration, the material obtained was assayed for kaempferol 3-gentiobioside by high performance liquid chromatography with the following conditions.

Apparatus: Liquid chromatograph
Pump: Pump LC-10AD (Shimazu)
Detector: SPD-10AV (Shimazu)
Printer: C-R8A CHROMATOPAK (Shimazu)
Column: YMC-Pack ODS-A (YMC)
Mobile phase: Diluted glacial acetic acid (1→80): acetonitrile (4:1) (used after degassing by ultrasonication)
Flow rate: 1.0 mL/min
Temperature: Room temperature
Detection: UV at 349 nm
Chart speed: 1 cm/min
Injection volume: 10 μL The assay showed that the mature leaf of *Cassia alata* contained about 1.8% of kaempferol 3-gentiobioside.

EXAMPLE 4

Histamine Release Inhibition

1. Objective

The objective of this example is to investigate histamine release inhibiting effect of a sample for determining its antiallergic effect or allergens, as well as to give an index for evaluating sample quality.

2. Experimental method

A mast cell suspension is collected from a rat abdominal cavity. The suspension is treated with a sample adjusted to 1 to 0.01% (specimen) and to the mixture is added a histamine releasing agent. Inhibition of this release is observed to determine an activity value.

3. Procedure

Inhibition of histamine release from mast cells from the rat abdominal cavity by Concanavalin A.

A solution of sample adjusted to a concentration of 0.01 to 0.003% in Tyrode's solution containing phosphatidyl-L-serine (PS) (1.75 mL) was preincubated at 37° C. for 5 min. To the solution was added 0.05 mL of the mast cell suspension from the rat abdominal cavity and the mixture was preincubated for further 15 min. Then, 0.2 mL of Concanavalin A solution in Tyrode's solution containing PS ($4 \times 10^{-4}$ g/mL) was added and the reaction was continued at 37° C. for 10 min. A control was prepared as described above except that 1.75 mL of Tyrode's solution containing PS was used in place of 1.75 mL of the sample solution in Tyrode's solution containing PS and 0.2 mL of Tyrode's solution containing PS was used in place of 0.2 mL of the Concanavalin A solution in Tyrode's solution containing PS. After quenching the reaction by ice cooling, the mixture was centrifuged at 300×g and 4° C. for 10 min. The amounts of histamine were determined for the supernatant and the sediment, respectively, according to the method of Shore et al. to calculate an inhibition rate to histamine release.

Calculation equation for a histamine release rate $$\text{Histamine release rate } (\%) = \frac{PS}{PS + PR} \times 100$$

PS=Amount of histamine in the supernatant
PR=Amount of histamine remaining in the cells
Calculation equation for a release inhibition rate $$\text{Inhibition rate } (\%) = 100 - \frac{S-B}{C-B} \times 100$$

S=Release rate of the sample
C=Release rate of the control
B=Blank

Preparation of a Suspension of Mast Cells From a Rat Abdominal Cavity.

A male Wistar rat weighing 300 to 500 g was sacrificed by exsanguination by decapitation and 15 mL of Tyrode's solution was injected in its abdominal cavity. After gently massaging the abdomen for about 90 sec, the abdomen was opened to collect an abdominal fluid. After further washing the abdominal cavity with 15 mL of Tyrode's solution, the washing was combined with the above abdominal fluid. The abdominal fluid was centrifuged at 55×g and 4° C. for 8 min, the supernatant was removed and rat abdominal cells were collected as a sediment. The cells were centrifuged at 265×g and 4° C. for 15 min and the supernatant was gently removed with an aspirator. The cells were washed with 3 mL of Tyrode's solution and centrifuged at 55×g and 4° C. for 8 min to provide mast cells as a sediment, which was then diluted with Tyrode's solution containing PS to adjust the mast cell concentration to about $1 \times 10^5$/mL.

Preparation of the Buffer

Tyrode's solution (pH 7.4) was prepared as follows.

An aqueous solution NaCl (137 mM), KCl (2,7 mM), HEPES (10 mM), $CaCl_2$ (1.6 mM), $NaH_2PO_4$ (0.41 mM), $MgCl_2$ (1 mM), glucose (0.1%) and gelatin (0.05%) was prepared, diluted with water to 1000 mL and was adjusted to pH 7.4.

Results

Inhibition of histamines release from mast cells from a rat abdominal cavity

| Sample | Concentration (g/mL) | Inhibition rate (%) |
|---|---|---|
| Flavonoid glycoside represented by formula I* | $9 \times 10^{-5}$ | 98.4 |
|  | $3 \times 10^{-5}$ | 28.5 |

*Releaser: Compound 48/80

The results show that the present compound exhibits an excellent effect even in a small amount.

As described above, it can be concluded that the flavonoid glycoside according to this invention has an excellent anti-allergic effect. The flavonoid glycoside can be extracted from a plant in Cassia genus, particularly from *Cassia alata* and its young leaves in a large amount. It may allow the flavonoid glycoside to be produced and used as an antiallergic agent with a lower cost.

What is claimed is:

1. An antiallergic composition comprising a flavonoid glycoside represented by formula I as a major component of the composition

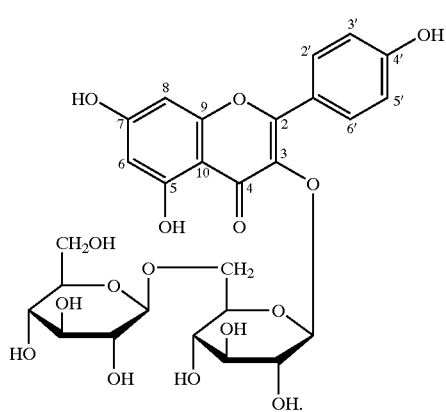

2. The antiallergic agent according to claim 1, wherein the compound represented by formula I is collected from a plant in Cassia genus.

3. The antiallergic agent according to claim 2, wherein the compound represented by formula I is collected from *Cassia alata*.

4. The antiallergic agent according to claim 1, wherein the compound represented by formula I is collected from young leaves of a plant in Cassia genus.

5. A food, drug, or cosmetic, comprising:
an antiallergenic effective amount of a flavonoid glycoside represented by formula I

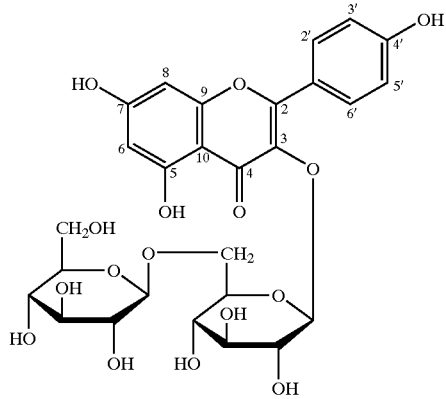

6. The product of claim 5, wherein the flavonoid glycoside represented by formula I is collected from a plant in Cassia genus.

7. The product of claim 5, wherein the flavonoid glycoside represented by formula I is collected from young leaves of a plant in Cassia genus.

8. The product of claim 5, wherein the flavonoid glycoside represented by formula I is collected from *Cassia alata*.

9. A method of inhibiting histamine release, comprising:
administering to a mammal an antiallergenic effective amount of a flavonoid glycoside as identified in formula I

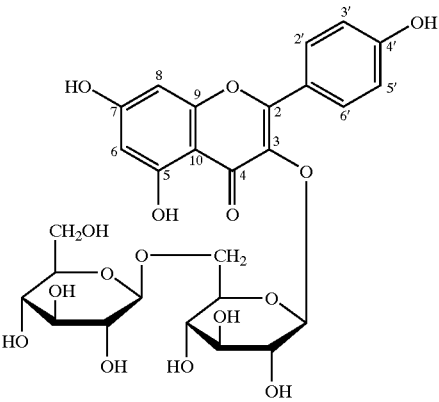

10. The method of claim 9, wherein the flavonoid glycoside represented by formula I is collected from a plant in Cassia genus.

11. The method of claim 9, wherein the flavonoid glycoside represented by formula I is collected from young leaves of a plant in Cassia genus.

12. The method of claim 9, wherein the flavonoid glycoside represented by formula I is collected from *Cassia alata*.

13. A method of obtaining a flavonoid glycoside represented by formula I, comprising:
extracting the flavonoid glycoside represented by formula I from a plant in Cassia genus

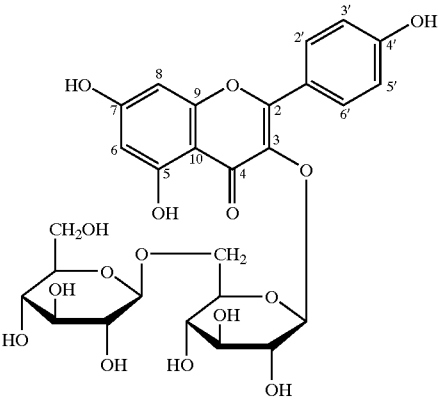

14. The method of claim 13, wherein the flavonoid glycoside is extracted from young leaves of a plant in Cassia genus.

15. The method of claim 13, wherein the flavonoid glycoside is extracted from *Cassia alata*.

* * * * *